US006896516B2

(12) United States Patent
Lin et al.

(10) Patent No.: US 6,896,516 B2
(45) Date of Patent: May 24, 2005

(54) REMOVAL PARTIAL DENTURE FREE OF PALATAL BAR OR LINGUAL BAR

(76) Inventors: Luh-Yuan Lin, 911 Tower Rd., Winnetka, IL (US) 60093; Jiin-Huey Chern Lin, 911 Tower Rd., Winnetka, IL (US) 60093; Chien-Ping Ju, 16 Pinewood Dr., Carbondale, IL (US) 62901

( * ) Notice: Subject to any disclaimer, the term of this patent is extended or adjusted under 35 U.S.C. 154(b) by 46 days.

(21) Appl. No.: 10/035,124

(22) Filed: Jan. 4, 2002

(65) Prior Publication Data

US 2003/0129563 A1 Jul. 10, 2003

(51) Int. Cl.[7] .............................................. A61C 13/00
(52) U.S. Cl. .................................... 433/167; 433/200.1
(58) Field of Search ................................ 433/178, 190, 433/200.1, 172, 167, 171, 199.1

(56) References Cited

U.S. PATENT DOCUMENTS

| 1,499,243 | A | * | 6/1924 | Nebeling et al. | 433/178 |
| 2,594,200 | A | * | 4/1952 | Mullere | 433/170 |
| 2,748,480 | A | * | 6/1956 | Weissman | 433/178 |
| 4,514,173 | A | * | 4/1985 | Re | 433/178 |
| 5,364,269 | A | * | 11/1994 | Willits et al. | 433/178 |

* cited by examiner

Primary Examiner—Todd E. Manahan
(74) Attorney, Agent, or Firm—Bacon & Thomas PLLC

(57) ABSTRACT

A removable partial denture that does not have a palatal or lingual bar, strap or plate connecting both sides of an arch of the partial denture. In addition to the rests and/or clasps, the partial denture is held in position by the shape of the linguoplate, which conforms to the shape of the lingual surface of the teeth and alveolar mucosa, and the shape of a portion of the adjacent gum tissue of the patient.

10 Claims, 3 Drawing Sheets

REMOVAL PARTIAL DENTURE FREE OF PALATAL BAR OR LINGUAL BAR

FIELD OF THE INVENTION

The present invention relates to removable partial dentures containing no lingual bar, and in particular to removable partial dentures containing no palatal bar or lingual bar for restoring teeth on the upper dental arch of a patient.

BACKGROUND OF THE INVENTION

Removable partial denture structures have been developed through the years to replace teeth which are missing through accident or disease. The conventional lower partial dentures have a major connector which is away from the healthy teeth of the patient, for examples mandibular continuous bar, mandibular lingual bar, mandibular lingual bar with continuous bar, mandibular linguoplate, mandibular continuous bar, creating voids between the teeth and the metal bar or similar structure, which cause a discomfort to the patient's tongue, and it becomes worse when food scrapes are stuck in the voids. The conventional partial dentures for restoring missing teeth on the upper dental arch of the patients have a bar, strap or plate as a major connector which connects the components on one side of the dental arch to the components on the opposite side thereof, for examples anterior-posterior palatal bars, single palatal strap type, U-shaped palatal major connector, and palatal plate-type major connector. The degree of discomfort is even more stronger for a patent wearing the conventional upper partial denture than who wearing the conventional lower partial denture, because the bar, strap or plate connecting both sides of the arch of the upper partial denture are right above the patient's tongue. There is a great need for a more comfortable removable partial denture for restoring teeth which are missing on the lower or, in particular, the upper dental arch of a patient.

SUMMARY OF THE INVENTION

The present invention involves a removable partial denture that does not have a palatal or lingual bar, strap or plate connecting both sides of an arch of the partial denture. In addition to the rests and/or clasps, it is held in position by the shape of the linguoplate, which conforms to the shape of the lingual surface of the teeth and alveolar mucosa, and the shape of a portion of the adjacent gum tissue of the patient.

The present invention discloses a partial denture in the form of an arch for restoring a tooth or teeth which are missing on one side of a dental arch of a patient comprising at least one denture tooth on one side of said arch, said at least one denture tooth being held by a resin material, said resin material being supported by a metal frame work of a metal casting, wherein said metal casting further comprises a linguoplate comprising a lingual portion, said lingual portion having a shape conformable to a shape of a lingual surface of teeth and alveolar mucosa from a tooth adjacent to said missing tooth or teeth to another tooth on another side of said dental arch of said patient for intimately contacting said lingual surface of said teeth and said alveolar mucosa; and a tissue portion extending from said lingual portion and having a margin 3–10 mm away from said lingual portion, said tissue portion having a shape conformable to a shape of a portion of a rear gum tissue connecting to said teeth and said alveolar mucosa, so that there is no gap between said teeth and said portion of said rear gum tissue not covered by said linguoplate; and said metal casting further comprises rests provided on said lingual portion of said linguoplate for engaging prepared notches on teeth of said patient.

Preferably, said tissue portion of the partial denture of the present invention further comprises a projection at said margin and on a side thereof facing said rear gum tissue, so that there is a space between said tissue portion and said portion of said rear gum tissue, when said partial denture is put on said dental arch of said patient.

Preferably, the partial denture of the present invention further comprises at least one denture tooth on another side of said arch for restoring a tooth or teeth which are missing on another side of said dental arch of said patient, which are held by a resin material supported by another metal frame work of said metal casting, wherein said another tooth on another side of said dental arch of said patient is a tooth adjacent to said missing tooth or teeth on another side of said dental arch of said patient Preferably, said lingual portion of said linguoplate of the partial denture of the present invention has a sharp occlusal edge approaching to an occlusal surface of said teeth of said patient, and said lingual portion of said linguoplate does not interfere an occlusion of said teeth of said patient, wherein said projection at said margin of said tissue portion of said linguoplate has a height of 0.5–3 mm.

Preferably, said linguoplate of the partial denture of the present invention contains no bar or strap connecting both sides of said arch.

Preferably, said metal casting of the partial denture of the present invention further comprises one or more clasps for engaging with one or more teeth of said patient.

Preferably, the partial denture of the present invention is for use in the upper dental arch of said patient.

The present invention also provides a method of restoring a tooth or teeth which are missing in the upper dental arch of a patient comprising aligning the partial denture of the present invention with the upper dental arch of said patient, and putting said partial denture on the upper dental arch of said patient, so that said lingual portion of said linguoplate intimately contacts said lingual surface of said teeth and said alveolar mucosa, said tissue portion of said linguoplate covers said rear gum tissue connecting to said teeth and said alveolar mucosa, said rests of said linguoplate are engaged with said notches on said teeth of said patient, and said missing tooth or teeth are restored by said at least one denture tooth, wherein there is a space between said tissue portion and said portion of said rear gum tissue.

A partial denture made according to this invention has a linguoplate which intimately attaches to the teeth and alveolar mucosa, but does not impinge on the portion of the gum tissue, avoiding the discomfort caused by the lingual bar, and the bar, strap or plate connecting both sides of an arch of the partial denture.

Another advantage to this invention is that by not having the palatal or lingual bar, strap or plate connecting both sides of an arch of the partial denture clasps, food cannot become entangled between the metal frame work and the teeth/gum tissue. Further, the abutment teeth preparation is almost eliminated, and the occlusal rest preparation is also minimal.

The partials made according to this invention are made by the conventional method, but preferably using Ti or Ti alloy to cast the metal frame work.

DETAILED DESCRIPTION OF THE PREFERRED EMBODIMENTS

Figure 1:
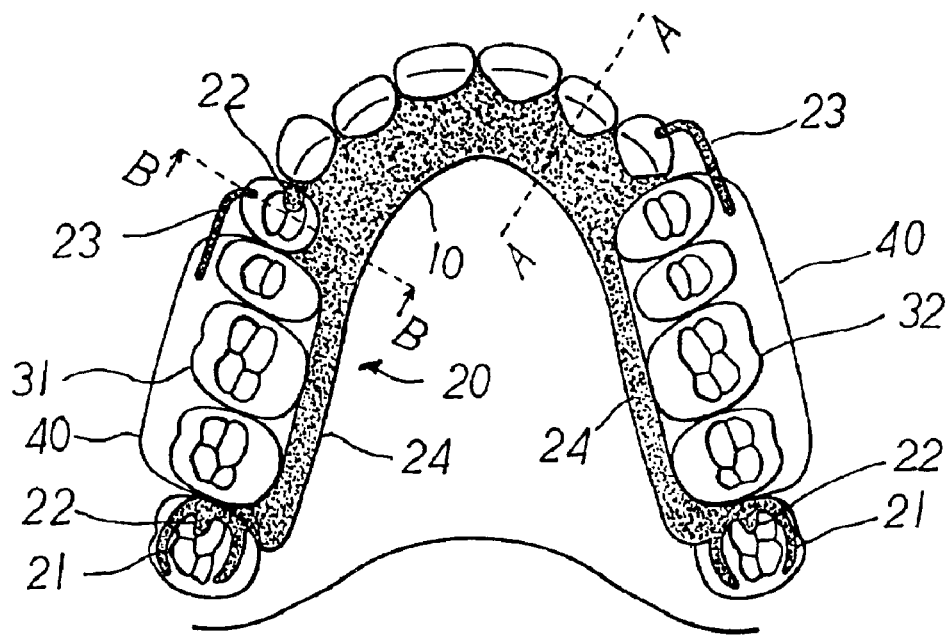
FIG. 1 is a perspective view of a removable upper partial denture according to a first preferred embodiment of the present invention from the occlusal aspect.

FIG. 1 illustrates a removal partial denture constructed according to a first preferred embodiment of the present invention, where the teeth missing on both sides of the dental arch of a patient are restored. It contains the denture teeth 31 and 32; the resin material 40; and a metal casting 20. The metal casting 20 is composed of two circumferential clasps 21, three occlusal rests 22, two bar clasps 23, a linguoplate 10, and two metal frame works 24, wherein a portion of the two metal frame works 24 are embedded in the resin material 40, and can not seen in FIG. 1. The resin material 40 bond the denture teeth 31 and 32 to the underlying metal frameworks 24. The circumferential clasps 21 hold onto the natural teeth at both ends of the dental arch. The occlusal rests 22 and the bar clasps 23 fit into the under cut area of the labial or buccal surface of in the natural teeth. The linguoplate 10 contacts all the teeth between the two denture teeth 31 and 32.

Figure 1A:
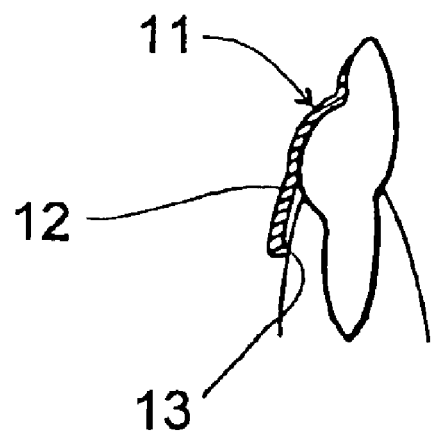
FIG. 1a is a partial cross sectional view taken along the line A—A shown in FIG. 1.
Figure 1B:
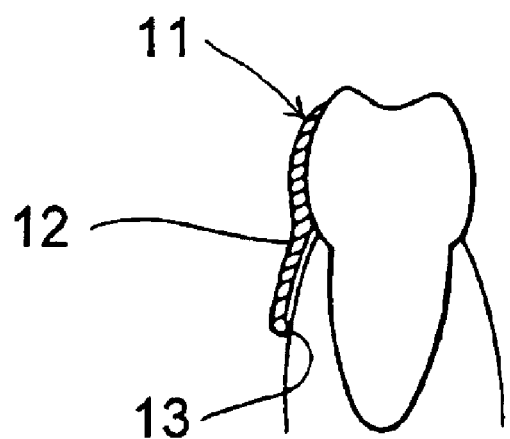
FIG. 1b is a partial cross sectional view taken along the line B—B shown in FIG. 1.

As shown in FIGS. 1a and 1b, the linguoplate 10 has a lingual portion 11, and said lingual portion 11 has a shape conformable to a shape of a lingual surface of the teeth and alveolar mucosa, and intimately contacts said lingual surface of said teeth and said alveolar mucosa, when the partial denture is put on said dental arch of said patient. The linguoplate 10 also has a tissue portion 12 extending from said lingual portion 11 and having a margin 3–10 mm away from said lingual portion. The tissue portion 12 has a shape conformable to a shape of a portion of a rear gum tissue connecting to said teeth and said alveolar mucosa, so that there is no gap between said teeth and said portion of said rear gum tissue, which is not covered by said linguoplate 10. Moreover, the tissue portion 12 has a projection 13 at said margin and on a side thereof facing said rear gum tissue, so that there is a space between said tissue portion 12 and said portion of said rear gum tissue, wherein said projection 13 acts as a seal. The lingual portion 11 of said linguoplate has a sharp occlusal edge approaching to an occlusal surface of said teeth of said patient, provided that the lingual portion 11 of said linguoplate does not interfere an occlusion of said teeth of said patient. The projection 13 at said margin of said tissue portion of said linguoplate has a height of 0.5–3 mm.

Figure 2:
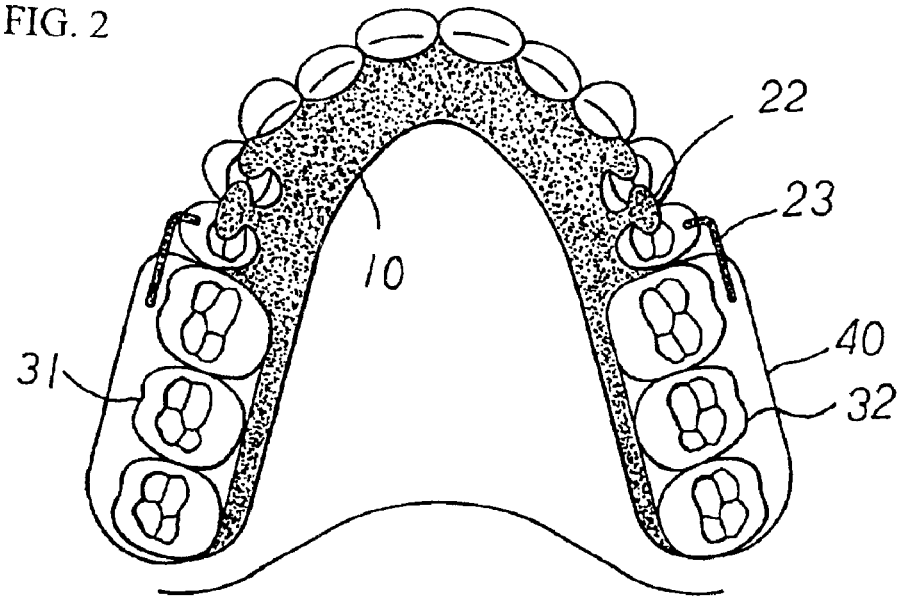
FIG. 2 is a perspective view of a removable upper partial denture according to a second preferred embodiment of the present invention from the occlusal aspect.

FIG. 2 illustrates a removal partial denture constructed according to a second preferred embodiment of the present invention. The partial denture of FIG. 2 is similar in construction to FIG. 1. Similar parts or elements are represented by common numerals with FIG. 1. In this embodiment, the teeth missing are on respective ends of the dental arch of a patient, so that the clasps 21 in FIG. 1 are omitted and additional occlusal rests 22 are provided on the linguoplate 10.

As shown in the embodiments of FIGS. 1 and 2, the linguopiate 10 extends from near one end of the dental arch to near another end of the dental arch.

Figure 3:
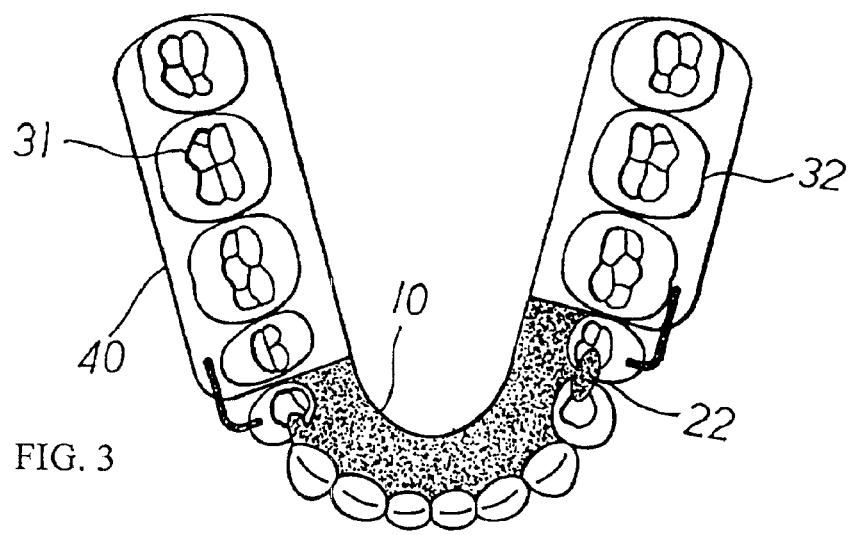
FIG. 3 is a perspective view of a removable lower partial denture according to a third preferred embodiment of the present invention from the occlusal aspect.

FIG. 3 illustrates a removal partial denture constructed according to a third preferred embodiment of the present invention. The partial denture of FIG. 3 is similar in construction to FIG. 2. Similar parts or elements are represented by common numerals with FIG. 2. In this embodiment, the teeth missing are on the lower dental arch of a patient and a less number of occlusal rests 22 are provided on the linguoplate 10 due to a less number of healthy teeth between the denture teeth 31 and 32.

Figure 4:
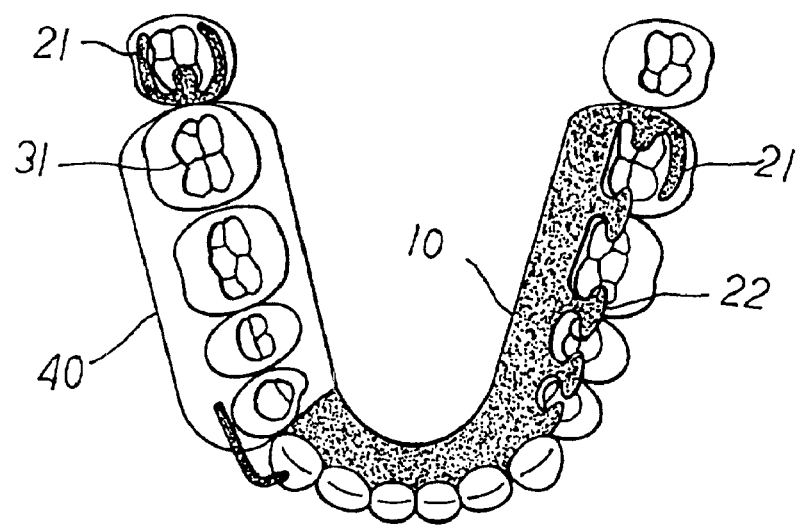
FIG. 4 is a perspective view of a removable lower partial denture according to a fourth preferred embodiment of the present invention from the occlusal aspect.

FIG. 4 illustrates a removal partial denture constructed according to a fourth preferred embodiment of the present invention. The partial denture of FIG. 4 is similar in construction to FIG. 3, except that the denture teeth 31 and the resin material 40 are provided only on one side of the partial denture, and the linguoplate 10 extends to another side of the partial denture of FIG. 4. Further, two clasps 21 and total five occlusal rests 22 are provided on the linguoplate 10 in FIG. 4.

The method of construction the partial denture of the present invention begins with impressions of the upper and lower dental arches of the patient. The impressions are then poured up in dental stone. On these stone models, metal castings 20 are made and denture teeth 31 and 32 are waxed into position to occlude with the opposing arch. The stone models together with the denture teeth 31 and 32 are waxed into position and are invested in dental plaster in dental flasks. When the plaster is set hard, the flask is placed in boiling water to remove the wax. When the upper part of the flask that contains the denture teeth 31 and 32 is removed from the lower flask that contains the metal casting 20 on the stone model of the patient's dental arch, there is a void where the wax was removed. Into this void is packed the dental resin material 40, and the upper and lower halves of the dental flask are placed in a dental clamp to hold the halves of the dental flask together while the flask and dental clamp are placed in boiling water for a period of time to process the dental resin dental material 40 to the denture teeth 31 and 32 and the metal frameworks 24.

The process of preparing the metal casting 20 includes preparation of the dentition, production of an impression, pouring of a model, waxing of the desired shape, investing the wax pattern, bum-out and heating, melting and casting Ti or Ti alloy, finishing and polishing, and heat treatment. The thickness of the wax is between 0.50 to 0.65 mm.

What is claimed is:

1. A partial denture in the form of an arch for restoring a tooth or teeth which are missing on one side of a dental arch of a patient comprising at least one denture tooth on one side of said arch, said at least one denture tooth being held by a resin material, said resin material being supported by a metal frame work of a metal casting, wherein said metal casting further comprises a linguoplate comprising a lingual portion, said lingual portion having a shape conformable to a shape of a lingual surface of teeth and alveolar mucosa from a tooth adjacent to said missing tooth or teeth to another tooth on another side of said dental arch of said patient for intimately contacting said lingual surface of said teeth and said alveolar mucosa, the linguoplate extends from near one end of the arch to near another end of the arch;

a tissue portion extending from said lingual portion and having a margin 3–10 mm away from said lingual portion, said tissue portion having a shape conformable to a shape of a portion of a rear gum tissue connecting to said teeth and said alveolar mucosa, so that there is no gap between said teeth and said portion of said rear gum tissue not covered by said linguoplate, and wherein said tissue portion further comprises a protection at said margin and on a side thereof facing said rear gum tissue, so that there is a space between said tissue portion and said portion of said rear gum tissue, when said partial denture is put on said dental arch of said patient; and said metal casting further comprises rests provided on said lingual portion of said linguoplate for engaging prepared notches on teeth of said patient.

2. The partial denture according to claim 1 further comprising at least one denture tooth on another side of said arch for restoring a tooth or teeth which are missing on another side of said dental arch of said patient, which are held by a resin material supported by another metal frame work of said metal casting, wherein said another tooth on another side of said dental arch of said patient is a tooth adjacent to said missing tooth or teeth on another side of said dental arch of said patient.

3. The partial denture according to claim 1, wherein said lingual portion of said linguoplate has a sharp occlusal edge approaching to an occlusal surface of said teeth of said patient, and said lingual portion of said linguoplate does not interfere an occlusion of said teeth of said patient, wherein said projection at said margin of said tissue portion of said linguoplate has a height of 0.5–3 mm.

4. The partial denture according to claim 1, wherein said linguoplate contains no bar or strap connecting both sides of said arch.

5. The partial denture according to claim 2, wherein said linguoplate contains no bar or strap connecting both sides of said arch.

6. The partial denture according to claim 1, wherein said metal casting further comprises one or more clasps for engaging with one or more teeth of said patient.

7. The partial denture according to claim 4, wherein said partial denture is for use in the upper dental arch of said patient.

8. The partial denture according to claim 5, wherein said partial denture is for use in the upper dental arch of said patient.

9. A method of restoring a tooth or teeth which are missing in the upper dental arch of a patient comprising aligning a partial denture as claimed in claim 4 with the upper dental arch of said patient, and putting said partial denture on the upper dental arch of said patient, so that said lingual portion of said linguoplate intimately contacts said lingual surface of said teeth and said alveolar mucosa, said tissue portion of said linguoplate covers said rear gum tissue connecting to said teeth and said alveolar mucosa, said rests of said linguoplate are engaged with said notches on said teeth of said patient, and said missing tooth or teeth are restored by said at least one denture tooth, wherein there is a space between said tissue portion and said portion of said rear gum tissue.

10. A method of restoring teeth which are missing in the upper dental arch of a patient comprising aligning a partial denture as claimed in claim 5 with the upper dental arch of said patient, and putting said partial denture on the upper dental arch of said patient, so that said lingual portion of said linguoplate intimately contacts said lingual surface of said teeth and said alveolar mucosa, said tissue portion of said linguoplate covers said rear gum tissue connecting to said teeth and said alveolar mucosa, said rests of said linguoplate are engaged with said notches on said teeth of said patient, and said missing teeth are restored by said at least one denture tooth on one side of said arch and by said at least one denture tooth on another side of said arch of said partial denture, wherein there is a space between said tissue portion and said portion of said rear gum tissue.

* * * * *